United States Patent [19]

Rovira

[11] 4,401,406
[45] Aug. 30, 1983

[54] REMOTE THREE AXIS CABLE TRANSPORT SYSTEM

[76] Inventor: Miguel Rovira, 3954 Hartford, St. Louis, Mo. 63116

[21] Appl. No.: 202,724

[22] Filed: Oct. 31, 1980

[51] Int. Cl.³ .................. B66F 11/00; F16H 7/16
[52] U.S. Cl. ........................ 414/589; 414/749; 254/278; 242/117; 250/491.1; 74/89.2; 212/214
[58] Field of Search .............. 414/630, 749-753, 414/589, 7; 74/89.2, 89.21, 89.22, 479; 212/214-217; 73/618-620; 33/1 M; 254/278; 242/117; 250/491

[56] References Cited

U.S. PATENT DOCUMENTS

| | | | |
|---|---|---|---|
| 3,142,387 | 7/1964 | Minty | 212/214 |
| 3,344,933 | 10/1967 | Jelatis et al. | 212/214 X |
| 3,529,481 | 9/1970 | Budzyn | 74/89.21 |
| 3,536,194 | 10/1970 | Novak | 212/215 X |
| 4,035,839 | 7/1977 | Eggleton et al. | 73/618 |
| 4,327,596 | 5/1982 | Simon | 414/749 X |

Primary Examiner—Robert J. Spar
Assistant Examiner—Terrance L. Siemens
Attorney, Agent, or Firm—Rogers, Eilers & Howell

[57] ABSTRACT

An apparatus for accurately positioning an object such as a radiation probe within a defined three dimensional space has a pair of support bars extending along each of three perpendicular axes defining said space with bearing block supports slidably mounted along each set of support rods. A cable drive for each direction of movement is provided to move these bearing blocks including a drive motor, a drum assembly including a capstan and cable guide, a drive cable, and a plurality of pulleys spaced along the system to achieve a balanced movement of the system in the associated direction. The cable is aligned so that each section of its run is either perpendicular or parallel to its other sections and is arranged with the capstan and cable guide so that there is an increase of tension as the cable is reeled in and a decrease of tension as the cable is payed out to reduce the stretching of the cable as the apparatus is operated.

12 Claims, 17 Drawing Figures

REMOTE THREE AXIS CABLE TRANSPORT SYSTEM

BACKGROUND AND SUMMARY

There are many applications for a device which can accurately and quickly position an object at a preselected point within a defined three dimensional space. For many of these applications it is required that the machine not only be capable of placing the object at the preselected coordinates which correspond to the distance chosen but also that it be capable of repeating that position with the same degree of accuracy. It is further important that the same degree of accuracy be available near the upper and lower limits of the system's movement as well as near the central portion.

One application in which this type of accurate positioning is required is in making measurements of radiation for calibrating the dosages to be administered to a patient. In this particular application, a container of water is used to approximate the attenuation attributable to the human body and a probe is accurately positioned within the water at varying coordinates corresponding to the position of an organ or the like. A source of radiation is then directed at the probe for a specific period of time. The probe may then be used to measure the amount of radiation received and hence predetermine to a very accurate degree the amount of radiation that a body tissue at that same position will receive when exposed to the same radiation source. This calibration significantly enhances radiation therapy in that controlled and measured dosages may be administered to the specific tissue located at the specified position in the particular patient requiring the treatment.

In the prior art, there have been systems developed to achieve the positioning of a probe within a cubicle containing water. These prior art systems generally utilize one or more chain drive mechanisms for at least one direction of movement, with cable drives for the other directions of movements. Of these two types of drive mechanisms, the cable drive has been found to be much more accurate in both the initial movement of the system to a particular preselected position and also in repeating that preselected position after the system has moved away. Of course, chain drive mechanisms rely on a chain and sprocket assembly which is virtually impossible to align and operate in a reversing mode and over the full length of the system without some slack in the chain. As can be appreciated, any slack in the system results in inaccuracies in positioning. There is also a problem in any flexible drive chain as there is almost always a certain amount of play between the individual links of the chain as they are pivotally connected together. Thus, it has been found that a chain drive provides less than desirable accuracy for those applications where both initial and repeated positioning of an object at a preselected point is desired.

In the cable drives of the prior art, a drive motor drives a capstan with a shortened chain and sprocket with a drive cable wrapped at least partially around the capstan and threaded through a series of pulleys which connect the cable between the support and the movable parts of the system. Although many different cable stringing schemes are available in the prior art, most if not all of these suffer from some inaccuracy caused by a failure to maintain the cable in a straight line orientation between the reeling in and reeling out position on the pulleys, thereby resulting in parallel and perpendicular runs of the cable; and in equalizing the tension between the take-up and feed action of the capstan as the cable circulates through the system during movement. Thus, at one end of the system's movement a different tension may result in a different spacing between successive locations. Also, system operation results in varying stresses placed on varying portions of the cable which have a tendency to stretch the cable and destroy the system calibration and accuracy.

Applicant has succeeded in developing a system for accurately positioning an object at any preselected point within a defined three dimensional space which utilizes a cable drive for each direction of movement. Thus, applicant's positioning system is a significant improvement over the prior art in that no chain drive mechanism of any kind is required. Instead, a cable drive including a capstan and drive motor is provided for each of the direction of movement required to fully "map" each individual point located within the three dimensional space defined by the system. While different sorts of coordinate systems may be used to "map" this space, applicant's preferred embodiment uses the three perpendicular coordinates of the Cartesian coordinate system; or X, Y, and Z as they are commonly known.

Applicant has further enhanced his system by designing and developing a cable drive and pulley system where the capstan and cable have an equalized tension therebetween throughout the entire limits of cable movement and the cable is aligned in a straight line between the take-up and feed positions of the pulleys which results in parallel cable runs. By utilizing an equalized tension and parallel or perpendicular cable layout, the problems of cable stretching or binding experienced in the prior art cable drives has been eliminated. Indeed, in applicant's system it is not strictly necessary that pulleys be used but instead any posts or other pivot point could be used as long as the cable is maintained in parallel or perpendicular runs.

In applicant's preferred embodiment, the cable drives for the Y and Z axes are mounted in a single sub-assembly which is in turn supported for movement along the X axis. A Y carriage is supported perpendicularly from the Z axis and the probe is supported from the Y carriage. By cantilevering the Y support carriage from the Z axis, all of the cable drives and controls can be located at one side of the system. This provides obvious advantages for many applications as it reduces the amount of material in the system and the possibility of error and reflection of radiation. Virtually all of the components are made of Delrin TM or other type of translucent plastic with stainless steel support rods and Teflon TM linear bearings to withstand the continuous exposure to water and provide long and reliable service. The cable itself may be a rubber or plastic coated stainless steel cable which enhances the frictional contact with the pulleys and capstan drives. The drive motors may be digital stepping motors capable of being computer controlled and which provide a high degree of accuracy in positioning of the probe.

By using applicant's invention, extremely accurate positioning of a probe or other object can be achieved which has been heretofore unknown in the prior art. For example, applicant is presently constructing and supplying machines incorporating his invention which provide a positioning resolution to 0.1 millimeters in each direction of movement. It is expected that even greater accuracy could be achieved if required for a particular application other than that which applicant is presently supplying machines for. Applicant has broadly described his invention for purposes of illustration and it may be more fully understood by referring to the drawings and description of the preferred embodiment which follows.

DETAILED DESCRIPTION OF THE PREFERRED EMBODIMENT

Figure 1:
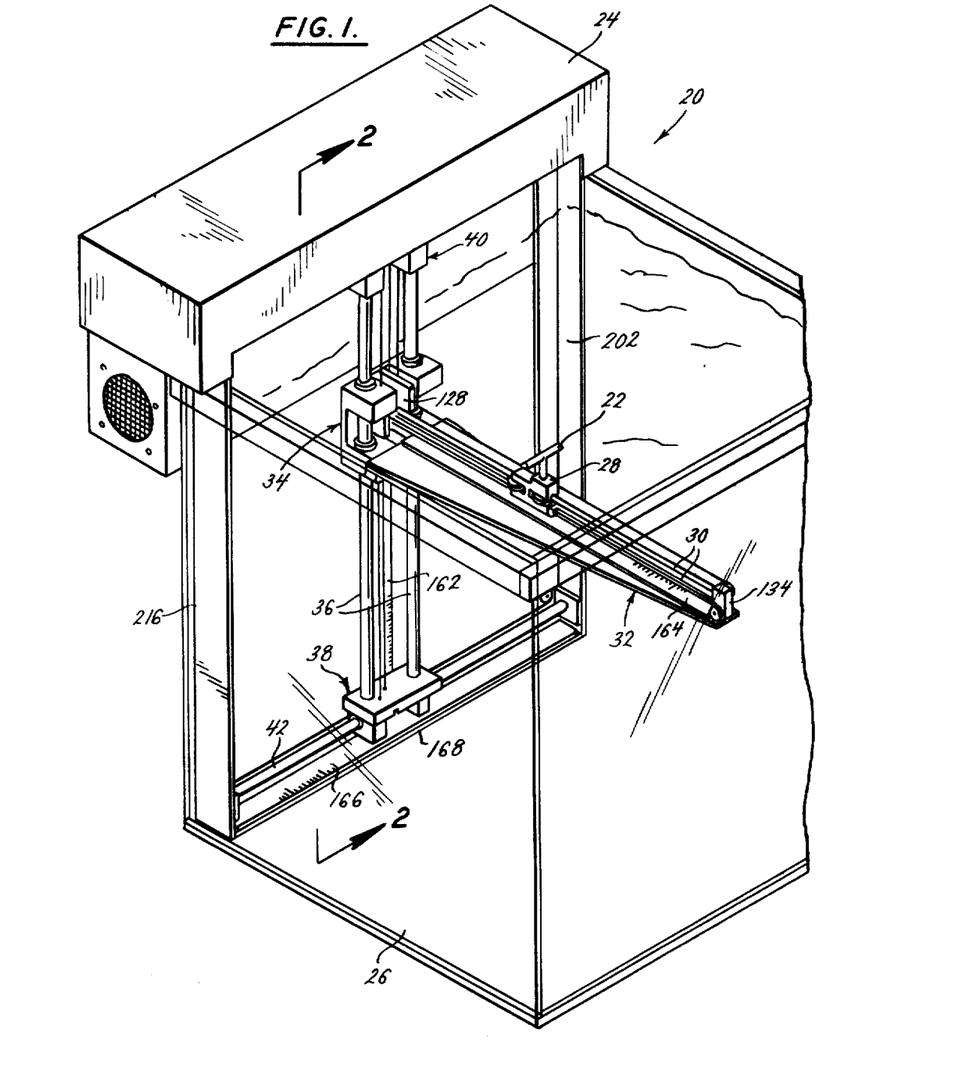
FIG. 1 is a perspective view showing applicant's cable drive and probe positioner immersed in a tank of water.

Applicant's cable transport system 20 is disclosed as part of a device to position a radiation probe 22 within a tank of water, as is shown in FIG. 1. However, it is to be understood that applicant's cable drive system may be used in a wide variety of applications and that this particular embodiment is being disclosed for purposes of illustration only.

As shown in FIG. 1, an enclosure 24 is supported from a side of the tank 26 and contains the drive motors, cable drive assemblies, and other drive structure for controlling the movement of each of three drive cables necessary to accurately position the probe 22 along the three axes X, Y, and Z. The probe 22 is mounted to a probe carrier assembly 28, which is in turn slidably supported on two probe rods 30. Probe rods 30 extend along the length of a horizontal carriage assembly 32 which is cantilevered from a Z-bearing block assembly 34. Movement of the probe 22 along the horizontal carriage assembly 32 will be defined as movement along the Y-axis.

The Z-bearing block assembly 34 is itself slidably supported on a pair of vertical support rods 36 which extend from a bottom bearing assembly 38 up to a top bearing assembly 40. As can be appreciated, the entire horizontal carriage assembly 32 can be moved vertically by moving the Z-bearing block assembly 34 along the vertical support rods 36, thus effecting a vertical movement of the probe 22 independently of its movement in the Y direction. Movement of the probe 22 in the vertical direction will be defined as movement in the Z direction.

The vertical support rods 36 are mounted to and extend between the top and bottom bearing assemblies 40, 38 which are themselves transportable in a transverse direction, independently of movement in the Y and Z directions. The bottom bearing assembly is slidably mounted on a bottom support rod 42 and the top bearing assembly is slidably mounted to a top support rod 44 (see FIGS. 2 and 3), such that the portion of the drive mechanism supported therefrom (including probe 22) can be driven as a unit in a transverse direction. Movement of the probe 22 in a transverse direction will be defined as movement in the X direction. Linear bearings 45 made of Teflon ™ or the like enhance the sliding movement of the various assemblies along the various support rods.

The movement of each of the above described assemblies, in each of the three directions X, Y, and Z, is achieved by a drive motor, driven assembly, and a drive cable which is routed through a series of pulleys for each direction of movement. The cable and pulley layout is shown schematically in FIG. 17, along with the drum assembly for each of the X, Y, and Z axes. Given this brief overview of applicant's invention, it will now be described in somewhat greater detail.

Figures 2, 7, 8, 9:
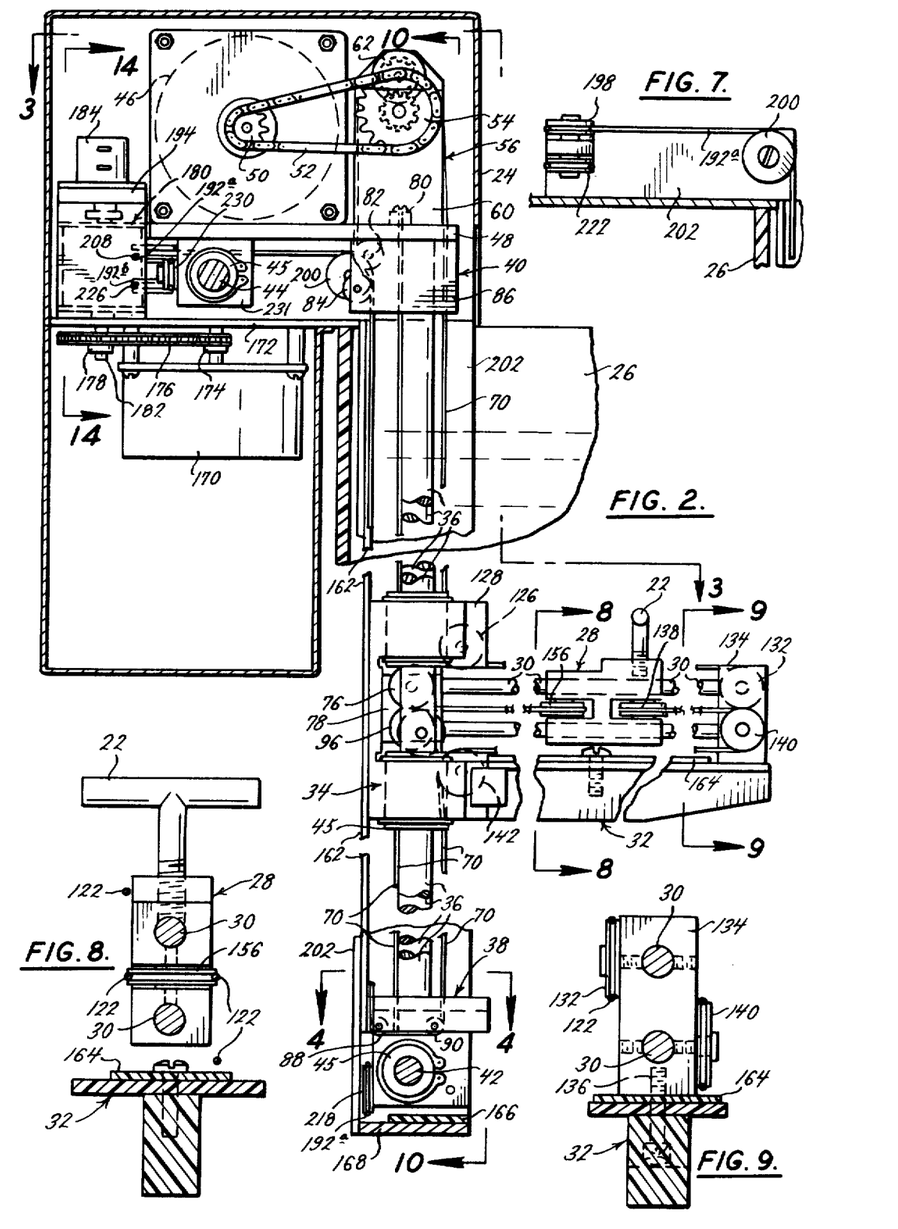
FIG. 2 is a cross-sectional view taken along the plane of line 2—2 in FIG. 1 partially broken away to detail the Z-cable drive, horizontal carriage assembly, and vertical support rods.
FIG. 7 is a cross-sectional view taken along the plane of line 7—7 in FIG. 3 and detailing the X-pulley mounting in the frame side panel.
FIG. 8 is a cross-sectional view taken along the plane of line 8—8 in FIG. 2 and detailing the probe carrier assembly.
FIG. 9 is a cross-sectional view taken along the plane of line 9—9 in FIG. 2 and detailing the front probe support assembly mounted on the horizontal carriage assembly.
Figures 10, 11, 12, 13, 14:
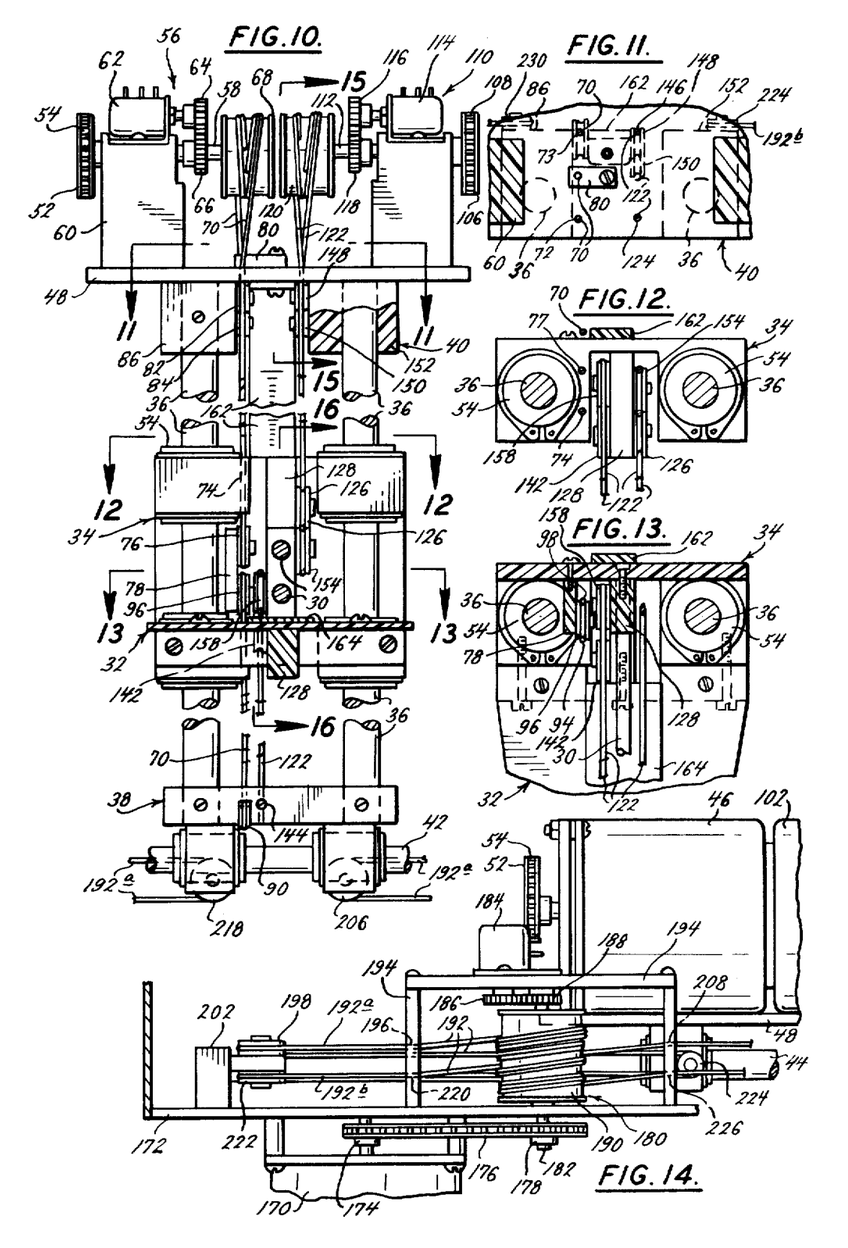
FIG. 10 is a cross-sectional view taken along the plane of line 10—10 in FIG. 2 which depicts a front view of the Y and Z drive motors, drive assemblies, top and bottom bearing assemblies, and Z-bearing block assembly.
FIG. 11 is a cross-sectional view taken along the plane of line 11—11 in FIG. 10 and detailing the pulley mounting at the top bearing assembly.
FIG. 12 is a cross-sectional view taken along the plane of line 12—12 in FIG. 10 and showing a top view of the Z-bearing block assembly.
FIG. 13 is a cross-sectional view taken along the plane of line 13—13 in FIG. 10 which further details the Z-bearing block assembly and rear probe assembly.
FIG. 14 is taken along the plane of line 14—14 in FIG. 2 and is a rear view of the X-drive motor and drum assembly.

Referring now to FIG. 2, enclosure 24 is shown in cross-section to house the Z-drive motor 46 mounted to the top plate 48 of top bearing assembly 40 and having a drive sprocket 50 with drive chain 52 serving as a driving connection to chain sprocket 54 on the Z-drum assembly 56. As shown in FIG. 10, the Z-drum assembly 56 has a drive shaft 58 rotatably supported by Z-drum stand 60 mounted to top plate 48 with a feedback potentiometer 62 mounted atop stand 60 and drivingly connected thereto through sprockets 64, 66. The Z- drum or capstan 68 is mounted to an end of Z-drive shaft 58 and has the Z-drive cable 70 wrapped therearound and extending downward through holes 72, 73 in top plate 48.

The Z-cable 70 path is shown schematically in FIG. 17, and will now be described in connection with the components shown in FIGS. 10–13. The forward end of Z-cable 70 extends through hole 72, as just mentioned and continues downward through hole 74 in Z-bearing block assembly 34 to wrap around the upper Z-pulley 76 rotatably mounted to Z-pulley support 78 and then back up through hole 77 in Z-bearing block assembly 34 to Z-end wire support 80 at the bottom of the top plate 48. As is best shown in FIG. 13, Z-pulley support 78 is mounted to the inside of Z-bearing block assembly 34.

The rear end of Z-cable 70 extends downward through hole 73 and is "pinched " between Z-pulleys 82, 84 rotatably mounted to left top block 86 and then extends all the way down to wrap around Z-pulleys 88, 90 (shown in the lower portion of FIGS. 2 and 4) rotatably mounted to bottom bearing assembly 38. Z-cable 70 then passes through hole 92 in bottom bearing assembly 38 and up through hole 94 in Z-bearing block assembly 34, around lower Z-pulley 96 of Z-pulley support 78, back down through hole 98 in Z-bearing block assembly 34, and is secured to bottom bearing assembly 38 by set screw 100.

Figure 3:
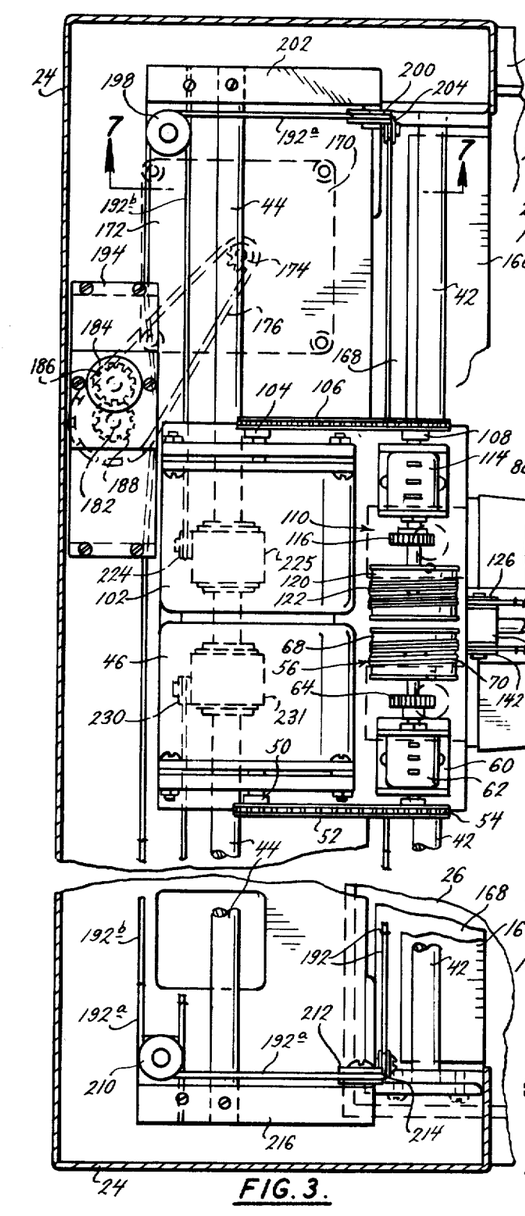
FIG. 3 is a cross-sectional view taken along the plane of line 3—3 in FIG. 2 which provides a top view of the drive motors, drum assemblies, and parts of the cable and pulley locations.

Referring now to FIGS. 3 and 10, the Y-drive motor 102 is similarly mounted to top plate 48 with drive sprocket 104 and drive chain 106 providing a driving connection to chain sprocket 108. The Y-drum assembly 110 is also mounted to top plate 48 and supports Y-drive shaft 112 driven by chain sprocket 108. A Y-feedback pot 114 is drivingly connected to Y-drive shaft 112 through sprockets 116, 118 and Y-capstan 120 is mounted at the outer end of Y-drive shaft 112. A Y-drive cable 122 drives the probe carrier assembly 28 along the horizontal carriage assembly 34 and is routed as shown schematically in FIG. 17. This routing will now be described in more detail in connection with FIGS. 2, and 8–12.

The Y-drive cable 122 is wrapped around the Y-capstan 120 and its forward end extends downward through hole 124 (FIG. 11) in top plate 48 to Y-pulley 126 mounted on rear probe assembly 128. Rear probe assembly 128 is secured to Z-bearing block assembly 34 by bolts 130, as is best shown in FIG. 16. Y-cable 122 wraps partially around Y-pulley 126 and extends horizontally along horizontal carriage assembly 34 to Y-pulley 132 on the front probe support assembly 134 bolted to the outer end of horizontal carriage assembly 34 by bolt 136 (FIGS. 3 and 9). After wrapping partially therearound, Y-cable 122 extends back along carriage assembly 34 to Y-pulley 138 on probe carrier assembly 28 and back to Y-pulley 140 on front probe support assembly 134 (FIGS. 3, 9). Y-cable 122 returns along carriage assembly 34 to Y-pulley 142 on rear probe assembly 128 and downward to terminate at Y-end wire support 144 in bottom bearing assembly 38 (FIG. 4).

Figure 4:
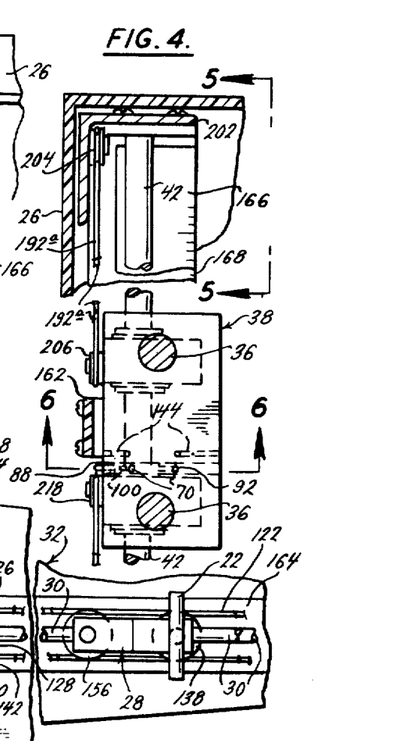
FIG. 4 is a cross-sectional view taken along the plane of line 4—4 in FIG. 2 and showing a top view of the bottom bearing assembly and side mount for the bottom support rod.

The rearward end of Y-cable 122 extends downward through hole 146 in top plate 48 and wraps partially around each of two closely spaced Y-pulleys 148, 150 (see FIG. 15) mounted on right top block 152 of the top bearing assembly 40. Y-cable 122 extends downward further to wrap around Y-pulley 154 mounted on rear probe assembly 128 and then horizontally along carriage assembly 32 to Y-pulley 156 in probe carrier assembly 28. Y-cable 122 then returns along carriage assembly 32 to wrap partially around Y-pulley 158 on rear probe assembly 128 and then extends downwardly where it terminates at Y-end wire support 144 on bottom bearing assembly 38.

The X-cable is somewhat more complicated then either the Z or Y drives as the top and bottom bearing assemblies 40, 38 must be moved in tandem and the top bearing assembly 40 supports the Z and Y drive motors 46, 102; Z and Y drum assemblies 56, 110; and their associated structure. To help maintain the top and bottom bearing assemblies 40, 38 aligned, and to measure the vertical position of the probe 22, a Z-rule assembly 162 is bolted to and extends between same (see FIG. 2). Similarly, Y-rule assembly 164 extends along the length of horizontal carriage assembly 32 and X-rule assembly 166 extends along the lower surface of the support frame 168.

The X-drive motor 170 is mounted to the upper frame support plate 172 and has drive sprocket 174 with drive chain 176 extending to chain sprocket 178 on X-drum assembly 180. As is best shown in FIGS. 2 and 14, unlike the Z and Y drum assemblies 56, 110, the X-drum assembly 180 is vertically aligned with its drive shaft 182 extending vertically through upper frame support plate 172. An X-feedback pot 184 is coupled to drive shaft 182 by sprockets 186, 188 thereabove. As is best shown in FIG. 14, the X-drum assembly 180 includes a capstan 190 around which is wrapped the X-cable 192. The X-capstan 190 is a double capstan, and there is an upper X-cable 192a and a lower X-cable 192b wrapped around the upper and the lower half thereof, respectively. A cover 194 is bolted to the upper frame support plate 172 and surrounds the X-capstan 190 to guide the X-cable 192 as it leaves the X-capstan 190.

Figures 5, 6:
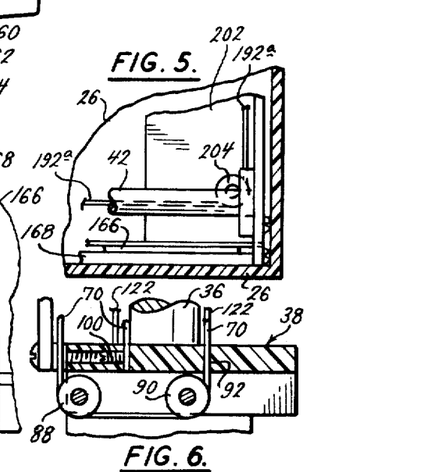
FIG. 5 is a cross-sectional view taken along the plane of line 5—5 in FIG. 4 and showing a front view of the side mounting of the bottom support rod.
FIG. 6 is a cross-sectional view taken along the plane of line 6—6 in FIG. 4 which details pulley mounting in the bottom bearing assembly.

The right hand side of X-cable 192a extends through hole 196, wraps partially around X-pulley 198 and extends forwardly to X-pulley 200, as is best shown in FIGS. 3 and 7. X-pulleys 198, 200 are mounted to the frame side panel 202. X-cable 192a extends downwardly from X-pulley 200 to X-pulley 204 and then transversely to X-pulley 206 mounted on bottom bearing assembly 38 before returning to terminate at a point just below X-pulley 204. See FIGS. 4 and 5.

The left hand side of X-cable 192a extends through hole 208 in cover 194 to X-pulley 210, and then forwardly to X-pulley 212 before extending downward to X-pulley 214. All of X-pulleys 210, 212, 214 are mounted to frame side panel 216, similarly to the right hand side of X-cable 192a. The left hand side of cable 192a extends transversely from X-pulley 214 to X-pulley 218 on bottom bearing block assembly 38 before returning to terminate at a point just below X-pulley 214.

The right side of X-cable 192b extends through hole 220 in cover 194 to X-pulley 222 mounted on upper frame support plate 172, back to wrap partially around X-pulley 224 mounted to the rear of right top block 152 and then back to terminate at a point near X-pulley 222. See FIGS. 11 and 14.

The left side of X-cable 192b extends through hole 226 in cover 194 out to X-pulley 228 (beneath X-pulley 210 in FIG. 3) mounted on frame side panel 216, back to wrap around X-pulley 230 mounted to the rear of left top block 86, and then back to terminate at a point near X-pulley 228.

Figures 15, 16, 17:
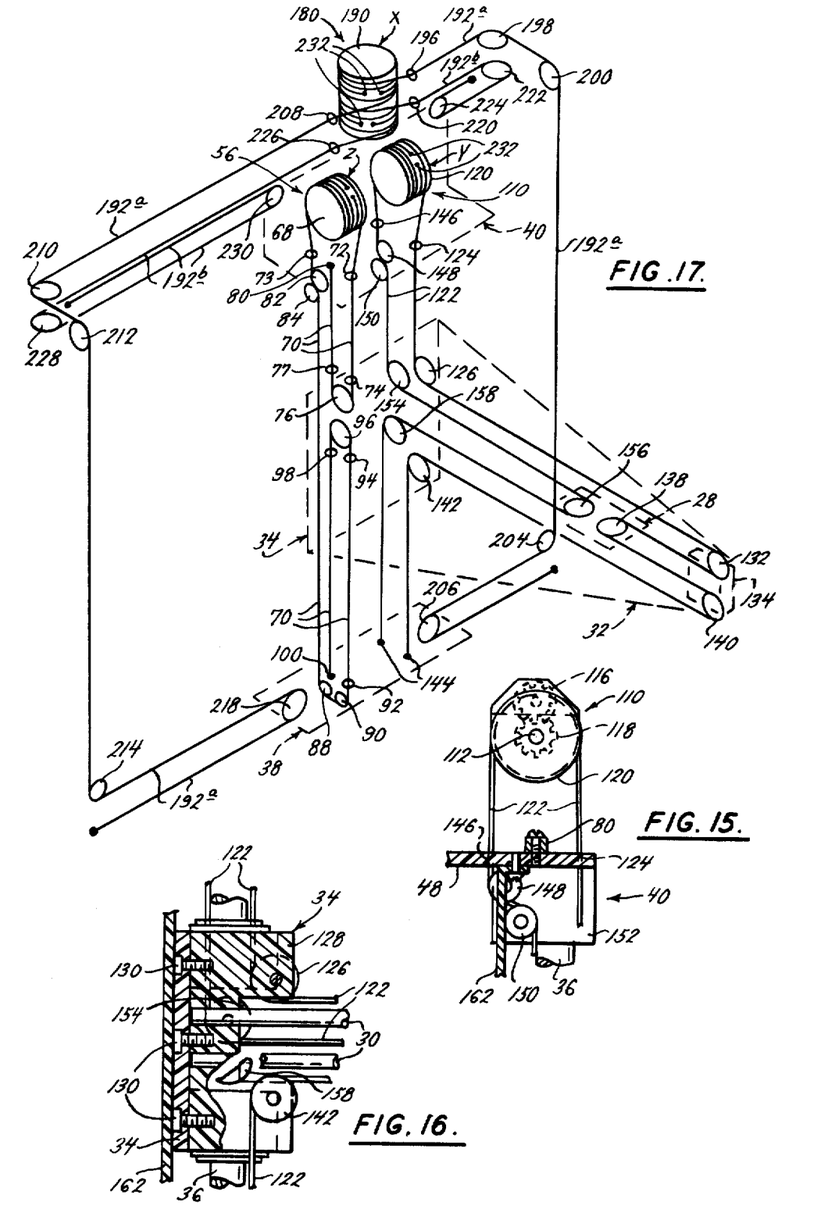
FIG. 15 is a cross-sectional view taken along the plane of line 15—15 in FIG. 10 which further details the Y-drum assembly.
FIG. 16 is a cross-sectional view taken along the plane of line 16—16 in FIG. 10 which further details the Z-bearing block assembly and rear probe assembly.
FIG. 17 is a schematic drawing, in perspective, showing the cable routing for all three directions of travel.

The entire cable routing for each of the cables 70, 122, 192a and 192b is shown schematically in FIG. 17. As represented therein, each cable may be cut in two, with each end thereof being separately secured to its respective capstan at a point 232. Cable installation is thus made easier, and error due to slippage and stretching is reduced.

Operation

Applicant's unique cable drive provides for the independent movement of the probe in any of the three directions: X, Y, or Z. The cable routing is shown generally in FIG. 17, but it should be noted that each cable is strictly parallel or perpendicular to itself as it runs from pulley to pulley from the capstan to its termination point. In addition, a strictly straight line is described by the cable as it leaves a pulley or guide hole and extends to the next pulley or termination point. Thus, there is no sideways flexing, twisting or torsioning of the cable. Furthermore, each cable is wrapped around its capstan such that the angle formed between the capstan and the guide hole increases as the cable is reeled in and also decreases as the cable is payed out so that the tension between the cable and the capstan does the same. This prevents stretching of the cable or otherwise placing stress thereon to reduce the amount of inaccuracy in the system as it is moved from one end of its travel to the other. A pair of pulleys are closely spaced in the Z and Y cable drives to take some tension off the capstans as the weight of the horizontal carriage assembly depends therefrom and would otherwise have a tendency to unwind these capstans and cause error.

Movement of the probe in each direction may be achieved as follows. Movement in the vertical or Z direction is controlled by the Z-capstan. As shown in FIG. 17, movement of the Z-capstan in a clockwise direction pays out the forward end of the Z-drive cable, thus lowering the Z-bearing block assembly. The rearward end of the Z-drive cable follows the movement of the forward end by shortening its length and thus pulling the Z-bearing block assembly in a downward direction through the various intervening pulleys. Thus, the Z-bearing block assembly is both lowered and pulled in the downward direction as the Z-capstan is rotated in the clockwise direction. The Y-capstan remains stationary, thus maintaining the length of the responsive ends of the Y-cable. However, movement of the Z-bearing block assembly is accommodated without affecting the positioning of the probe carrier assembly by the rotation of the various Y-pulleys located along the horizontal carriage assembly. Thus, the Y-pulleys serve as idler pulleys which merely follow the movement of the Z-bearing block assembly without affecting the position of the probe carriage assembly. Of course, the X-pulleys are not affected by any of the above.

Movement in the Y-direction, or along the horizontal carriage assembly, may be described as follows. If the Y-capstan is viewed as rotating in the clockwise direction, then the forward end of the Y-cable pays out at the same time that the rearward end of the Y-cable is reeled in. Thus, the probe carriage assembly is pulled closer to the Z-bearing block assembly, or in the negative direction. This is required as the probe carrier assembly is the only movable part of the system which supports a Y-pulley. Thus, as the rearward Y-cable is shortened, the probe carrier assembly must be moved along the probe rods closer to the Z-bearing block assembly. None of the other X or Z pulleys are affected by movement of the Y-capstan.

Movement along the X direction is achieved in much the same manner as that along the Y or Z direction. The Y and Z drive assemblies are self contained and supported by the top and bottom bearing block assemblies and vertical rods extending therebetween. The horizontal carriage assembly is of course supported from the Z-bearing block assembly slidably mounted on the vertical support rods and thus follows the movement of the top and bottom bearing block assemblies. Movement in the X direction may be explained by presuming that the X-capstan rotates in a clockwise direction. This pays cable out to the left and reels it in from the right. This corresponds to a movement of the entire Y and Z system to the right, or in the +Y direction. None of the other pulleys in the Y or Z cable systems are affected by movement in the X direction.

Various changes and modifications would be apparent to one of ordinary skill in the art. These are included within the teaching of applicant's invention and he intends that his invention be limited only by the scope of the claims appended hereto.

What is claimed is:

1. A system for accurately positioning a probe at any preselected point in a three dimensional space comprising: a probe, means defining a bounded three dimensional space including a support, said support having at least one guide bar extending along each of three directions of movement, and a guide block supported on each of said guide bars, said probe being mounted to one of said guide blocks, said system having means for selectively moving said probe in a plurality of directions including a cable drive for moving said probe in each movable direction, each of said cable drives including a motor and a cable means associated therewith, said cable means extending between said drive motors, guide blocks, and said support, each drive motor and cable means having a capstan associated therewith, each of said drive motors being in driving relation to its associated capstan, each cable means including at least one cable wrapped at least partially around its associated capstan so that rotation of a capstan by a drive motor causes said cable to move at least one guide block along its associated guide bar and thereby move the probe, and wherein a sub-assembly mounts the drive motors and capstans for two directions of movement, said sub-assembly being supported from at least one of said guide bars for said third directions of movement, said third motor for the third direction of movement and its associated capstan and drive cable having means to move said sub-assembly along its associated guide bar.

2. The system of claim 1 wherein said third capstan is a double capstan with twice the number of drive cables associated therewith as that of said first or second capstans, said sub-assembly being supported from a guide bar at both ends thereof by a guide block, one side of said third capstan driving the guide block at one end and the other side of said third capstan driving the guide block at the other end.

3. The system of claim 1 wherein said probe is sensitive to radiation, and said space is filled with water, said probe thereby measuring the attenuation of radiation caused by said water.

4. The system of claim 1 wherein each guide block has at least one pair of pulleys associated therewith for rotatably securing at least one drive cable thereto.

5. The system of claim 1 wherein each drive cable has an end fixedly secured to either said support or said guide blocks supporting either end of said sub-assembly.

6. The system of claim 5 wherein each drive cable has its other end fixedly secured to its associated capstan, each capstan having at least two drive cables associated therewith.

7. The system of claim 1 further comprising means to increase the tension between each of said cables and its associated capstan as the cable is reeled in and decrease said tension as the cable is payed out.

8. The system of claim 7 wherein each of said cable means includes a second cable wrapped at least partially around said capstan and opposing said first cable so that said second cable pays out as said first cable is reeled in, and means to increase the tension between said second cable and the capstan as it is reeled in and decrease said tension as it is payed out.

9. The system of claims 7 or 8 wherein said tensioning means includes a cable guide, said cable guide having means to slidably receive the cable means.

10. A system for accurately positioning a radiation sensitive probe at any preselected point in a three dimensional space filled with water comprising: a radiation sensitive probe, means defining a bounded three dimensional space including a bottom and sidewalls, said bottom and sidewalls being joined at their edges to form a watertight seal, means for supporting and moving said probe within said defined space including at least one guide bar extending in each of three directions along orthogonal coordinates, at least one guide block supported on each of said guide bars, the support bars extending in two of said three directions being supported by said guide blocks, said probe being slidingly mounted to the support bars extending in one of said directions, a cable drive for each of said three directions, each cable drive comprising a drive motor and a capstan operatively connected to said drive motor, a sub-assembly for mounting two of said cable drives, said third cable drive having means to move said sub-assembly along its associated guide bar, a cable means wrapped at least partially around each of said capstans, said cable means extending between said capstan, its associated guide blocks, and said space defining means.

11. The system of claim 10 wherein each cable drive further comprises a plurality of pulleys around which its associated cable means is at least partially wrapped.

12. The system of claim 11 wherein each cable means defines a straight line as it extends from one of said pulleys to another of said pulleys, each of said straight lines being either substantially parallel to or perpendicular to each of said other straight lines.

* * * * *